United States Patent [19]

Hariri

[11] Patent Number: 4,825,864
[45] Date of Patent: May 2, 1989

[54] MICROSURGERY TOOLS

[76] Inventor: Robert J. Hariri, 420 E. 70th St., New York, N.Y. 10021

[21] Appl. No.: 131,300

[22] Filed: Dec. 8, 1987

Related U.S. Application Data

[63] Continuation of Ser. No. 778,586, Sep. 20, 1985, abandoned, which is a continuation-in-part of Ser. No. 563,680, Dec. 20, 1983, abandoned.

[51] Int. Cl.$^4$ .............................................. A61B 17/00
[52] U.S. Cl. .................................................. 128/303 R
[58] Field of Search ............ 128/303 R, 305, 751–755, 128/92 VJ, 354, 355, 340; 7/167, 168, 125, 138, 158; 81/125.1, 437, 438, DIG. 5, 3.44, 415, 416, 427.5

[56] References Cited

U.S. PATENT DOCUMENTS

| | | | |
|---|---|---|---|
| 441,979 | 12/1890 | Rohrbach et al. | 7/138 |
| 510,981 | 12/1893 | Massey | 7/138 |
| 1,359,164 | 11/1920 | Lo Giudice et al. | 128/321 |
| 1,842,403 | 1/1932 | Hunsaker et al. | 128/355 |
| 2,803,252 | 8/1957 | Bloome | 128/354 X |
| 3,740,779 | 6/1973 | Rubricuis | 128/303 R X |
| 3,798,688 | 3/1974 | Wasson | 7/158 |
| 4,446,866 | 5/1984 | Davison | 128/321 X |

OTHER PUBLICATIONS

Mueller, "The Surgical Armamentarium", (1980), pp. 369, 554 and 748, A.V. 333.
Sklar Surgical Instruments Catalog (1973), p. 194, A.V. 333
Mueller, "A Comprehensive Guide to Purchasing", (1963), p. 469, A.V. 336.

*Primary Examiner*—Michael H. Thaler
*Attorney, Agent, or Firm*—Kuhn and Muller

[57] ABSTRACT

A bipolar microsurgical instrument enabling a surgeon user thereof to effect successive operative steps incident to microsurgical procedures while retaining the surgeon's position at a microscopic viewing port defining a field of vision wherein the instrument is being used to effect the procedures. The instrument comprises an elongated body the distal ends of which comprise first and second oppositely extending surgical tools which define alternate poles of the instrument. The first and second microsurgical tools are functionally distinct from one another, but are functionally related as to be sequentially utilizable by the surgeon in the microsurgical procedure in which the instrument is being employed. Accordingly, the surgeon may utilize the bipolar instrument by sequentially utilizing the first and second tools, while maintaining the same instrument continuously in hand, thereby eliminating the need to interchange instruments and/or to remove the eyes of the surgeon from the microscopic viewing port to thereby lose contact with the field of vision.

6 Claims, 1 Drawing Sheet

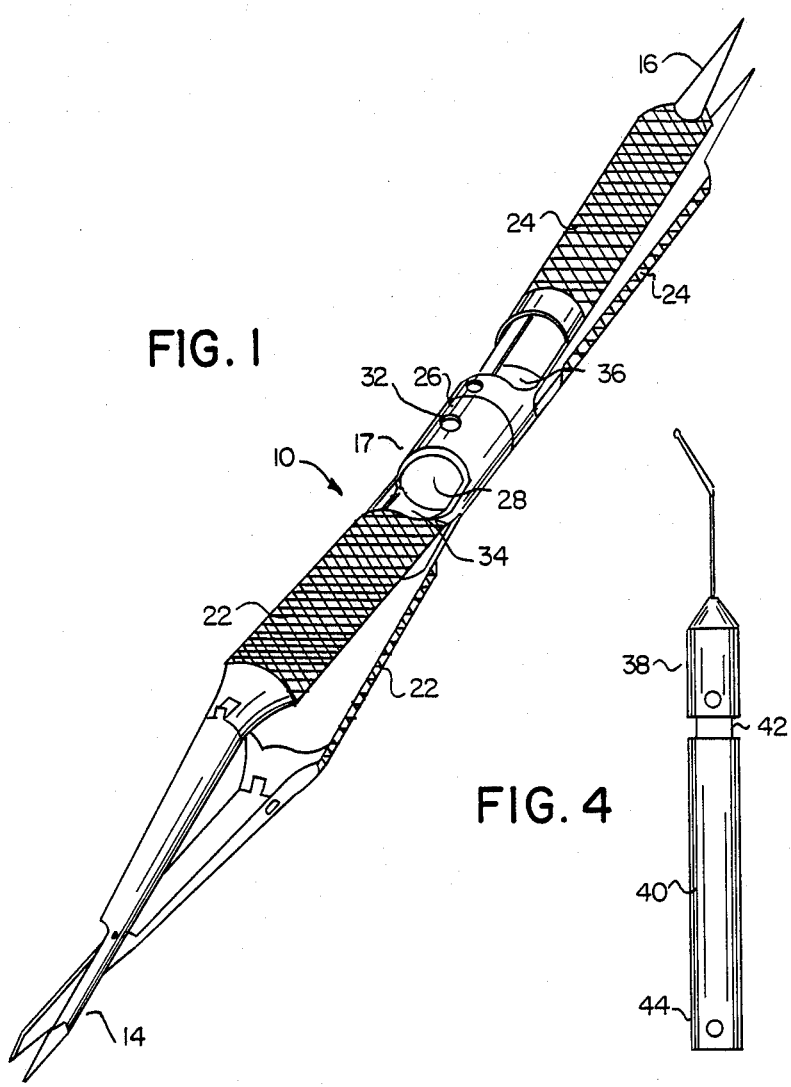
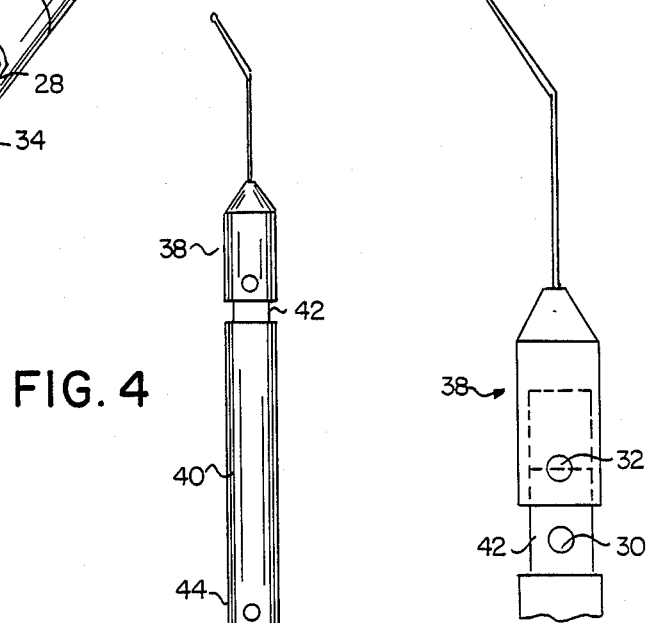
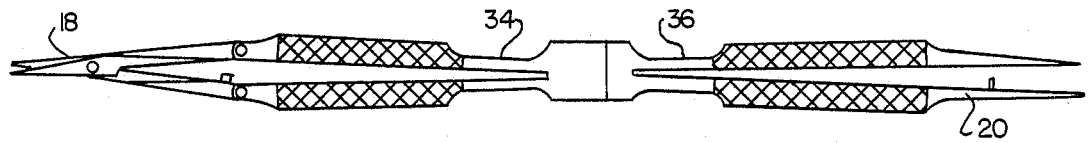
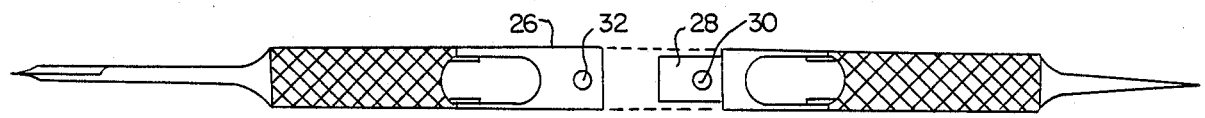

MICROSURGERY TOOLS

This application is a continuation of application Ser. No. 778,586 filed Sept. 20, 1985 now abandoned, which is a continuation-in-part of my co-pending application, Ser. No. 563,680, filed Dec. 20, 1983.

BACKGROUND OF THE INVENTION

This invention relates generally to surgical instruments and methodology, and relates more specifically to instruments specifically adapted for microsurgical medical procedures.

It is estimated that in the United States today, over 30,000 operations involving microsurgical techniques are performed annually. The techniques of microsurgery largely evolved in the areas of vascular and neurosurgery, and are used in bypass and brain tumor procedures. However, as the techniques have become established and better known, applications in other fields have appeared, and they are now common in opthamalogic surgery, reattachment of digits and limbs, in vasovasotomy procedures and in other surgical areas. In one reported study, non-microsurgical vasovasotomy (the repair of a vasectomy) had a success rate as measured by the presence of motile sperm in the ejaculate of only 5%. Dr. Marc Goldstein, Director of the Cornell Medical Center Urologic Microsurgery Unit, however, reported over 90% success using microsurgery.

Understanding of the present invention will be facilitated by a consideration of the conditions under which such procedures are carried out.

First, the tissues, vasculature or other area subject to the procedure are so minute that a binocular microscope is used, the magnification being typically in the range of 6 to 40 power. Generally speaking, individual tools used in these procedures are miniaturized versions of tools used in standard surgery. Unlike standard, gross-field surgical techniques, in which suture material ranges from stainless steel wire up to 24 gauge to 6-0 material and can be threaded or swaged to needles of significantly larger diameter, microsurgery requires the use of suture material directly swaged to needles from 50-100 microns in diameter and the suture itself is in the range of 8-0 (0.04 mm to 0.049 mm) to 11-0 (0.019 mm) in diameter.

Sure-handedness is the hallmark of the microsurgeon. In procedures that may last as long as ten hours, fatigue, eyestrain and irritation are factors which may impair a microsurgeon's ability to perform, and must be taken into account. Any means that will speed up a procedure is desirable, as is any means that will make the surgeon more comfortable as he or she carries out this exacting craft. More particularly, there is a natural tendency for the hands to move from their original orientation when a surgeon is not observing the position of the hands. The ability to maintain direct and continuous eye contact on hand position helps prevent accidental injury to tissue by inadvertent hand movement.

In order to better appreciate the severity of the aforementioned difficulty, it is important to understand that the type of binocular viewing system which is used by the surgeon during microsurgery techniques, bears but limited resemblance to the conventional device used in the laboratory, wherein specimens being observed are directly aligned with the viewer's axis of sight. In this conventional arrangement, the viewer thus looks through the binocular microscope at a sample which is positioned directly beneath and aligned with the longitudinal axis of the microscope. Accordingly, it is a relatively simple matter for the surgeon to remove or deflect his or her vision momentarily from the microscope to observe without the aid of same. Correlation of hand movements is simple in this instance too, in that the only effect actually achieved by the microscope is to amplify the field of vision, which in a sense is directly in front of the viewer to begin with.

However, in the instance of the type of sophisticated instrumentation used in microsurgery for viewing the area in which operations are being carried out, much more complex systems are involved, which are usually referred to as "surgical operating microscopes". Instruments of this type are available from several sources, including Carl Zeiss, Inc. of Thornwood, N.Y., and Wild Heerbrugg, Ltd., of Heerbrugg, Switzerland. In these highly sophisticated instruments, the binocular eyepieces are arranged at an angle up to 90° with respect to the objective lenses (indeed, several such binocular viewing ports may form part of a single operating microscope, so that several surgeons and/or assistants can view the operating field at one time). This arrangement is intentional in that it enables the surgeon to conduct procedures while standing in an upright position, or in a slightly leaning over position while the hands of the surgeon carry out the procedures in the operating zone. Thus, the surgeon, while looking through the binocular instrument and gazing upon the field of operation, is not in a position wherein the line of eyesight normally physically intersects the operating zone. The effect is as if the zone being viewed were not directly connected with the normal physical arrangement of viewing, and this in part accounts for the aforementioned difficulties of reorienting the instruments and hands to the operating zone in the event the surgeon physically removes his or her eyes from the microscope to observe other areas of the operating room, to grasp instruments from an attendant, or from a side platform, or so forth.

Pursuant to the foregoing, it would therefore be exceedingly desirable were the surgeon able to maintain his or her position at the viewing port of the binocular microscope as a change is made from one to another of the instruments, which may be sequentially utilized in the course of an operation. However, this has not heretofore been possible in that normal procedure has required to the contrary, that when instruments are sequentially utilized, the surgeon must change from a first to a second instrument, often necessitating removal of the surgeon's gaze from the operating field as aforementioned, with attendant loss of time and precision, and with the generation of fatigue and irritation.

While it has heretofore been known to provide double-ended surgical instruments, these full size instruments of the prior art have little or nothing to do with the problem to which the present invention is addressed. Thus, for example, the 1980 American Hospital Supply Corporation, American v Mueller Division catalogue, entitled "Surgical Armamentarium" illustrates at pages 369, 554 and 749 such double-ended instruments of the prior art. These instruments will be found to essentially constitute arrangements of like tools at each end of a single handle. There is no provision for interchangeability of the respective ends, and more significant, there is no relationship between the opposed ends of these tools, which is a criteria which is totally essential for use in a microsurgical instrument in order to meet the objectives of this invention.

Pursuant to the foregoing, it may be regarded as an object of the present invention, to provide a bipolar microsurgical instrument which enables a surgeon user thereof to effect successive operative steps incident to microsurgical procedures, while retaining the surgeon's position at a microscopic viewing port defining a field of vision wherein the instrument is being used to effect such procedures.

It is a further object of the invention, to provide an instrument as aforementioned, having interchangeability aspects with respect to the tools on the bipolar instrument; and wherein the interchangeable features are specifically related to the sequential use of the instruments thus joined.

It is yet a further object of the invention, to provide a kit for assembling therefrom a determinatively configured bipolar surgical instrument, which enables the user to effect successive operative steps incident to microsurgical procedures while retaining the surgeon's position at a binocular microscopic viewing port as aforementioned.

SUMMARY OF INVENTION

Now in accordance with the present invention, the foregoing objects and others as will become apparent in the course of the ensuing specification are achieved in a bipolar microsurgical instrument, which enables the surgeon user to effect successive operative steps incident to microsurgical procedures, while retaining the surgeon's position at the microscopic viewing port defining a field of vision wherein the instrument is being employed.

According to the invention, the bipolar instrument includes an elongated body, the distal ends of which comprise first and second oppositely extending surgical tool means which define alternate poles of the instrument. The first and second microsurgical tool means are functionally distinct from one another, but are functionally related as to be sequentially utilizable by the surgeon in the microsurgical procedure in which the instrument is being employed. Accordingly, the surgeon may utilize the instrument by sequentially employing the first and second tool means thereof, while maintaining the same instrument continuously in hand, thereby eliminating the need to interchange instruments and/or to remove the eyes of the surgeon from the microscopic viewing port—which would cause loss of contact with the field of vision.

The first and second tool means preferably include base portions which are removably interlockable with one another, to define when interlocked a central cylindrical portion of the instrument. This interlock feature enables the tool means to be interchanged with other combinations of tool means to provide plural functional possibilities for the instrument.

Preferably, the base of one of the first and second tool means is a male connector and the base of the other a female connector, the two bases being mateable to effect the mentioned interlock.

The respective bases of the first and second tool means are cylindrical and adjoin ovoid-shaped depressions, said depressions flanking the central cylindrical portion of the bipolar instrument to provide tactile indicia means for the surgeon, to aid the latter in centering and rotating the instrument during use of same.

The first tool means in the aforementioned combinations preferably comprises a forceps or a needle holder. The second tool means comprises a scissors or a microprobe. The combination of first and second tool means, as aforementioned, are sequentially related in the surgical procedures normally incident in the field to which the invention apertains.

In another aspect of the invention, a kit is provided for assembling therefrom a determinatively configured bipolar surgical instrument as aforementioned. The kit comprises a set of first microsurgical tools each of which terminate in a male connecting base as aforementioned; and a set of second microsurgical tools each of which terminates in a female connecting base. These sets are in accordance with the prior discussion; i.e. one set includes a forceps and a needle holder, the second set includes a scissors and a microprobe.

The kit as aforementioned, preferably further includes an elongated extension piece, the alternate ends of which respectively comprise male and female connectors mateable with the bases of the first or second tool means. This enables by assembly with a selected first or second tool means, a uni-polar microsurgical instrument based on the selected tool means.

BRIEF DESCRIPTION OF DRAWINGS

The invention is diagramatically illustrated, by way of example, in the drawings appended hereto, in which:

FIG. 1 is a perspective view of a bipolar microsurgical instrument in accordance with the present invention;

FIG. 2 is a side elevational view of the instrument of FIG. 1, showing same when assembled;

FIG. 3 is a side elevational view of the instrument of FIGS. 1 and 2, but showing the instrument in disassembled arrangement;

FIG. 4 is a side elevational view, showing an arrangement wherein one of the unipolar ends of the aforementioned instruments is associated with an extension piece to provide a unipolar instrument in accordance with one aspect of the invention; and FIG. 5 is an enlarged view of the forward end of the device of FIG. 4, showing in further detail the association of the respective parts.

DESCRIPTION OF PREFERRED EMBODIMENT

In FIG. 1 herein, a perspective view appears of a bipolar microsurgical instrument 10 in accordance with the present invention. The instrument 10 is seen to comprise generally, an elongated body 12, the distal ends of which comprise first and second oppositely extending surgical tool means 14 and 16. As better seen in the views of FIGS. 2 and 3, in the present instance the tool means 14 comprises a microscissors 18, and the tool means 16 comprises a micro-forceps 20. In accordance with the invention, the micro-scissors can comprise any type known in the art, i.e. curved and straight; and the microforceps can be of types previously known, except that preferably the forcep is provided with the platform for tying, a highly polished and tapered dilating surface, and optionally with micro-teeth. Each of the tool means 14 and 16 are formed of stainless steel or the like and are provided at their mid-range portions with pairs of articulated knurled grasping portions 22 and 24.

Each tool means terminates at a cylindrical base portion 26 and 28. The base portion 26 of tool means 14 is female, the base portion 28 of tool means 16 is a projecting male portion 28. As best seen in the disassembled view of FIG. 3, the male based portion 28 is provided with a spring biased projecting pin 30, which once the base 28 is mated with base 26, is received within the opening 32 transversely formed in the wall of base 26, so that when the respective tool means are adjoined, a full interlock is provided to yield the final configuration, as shown in FIGS. 1 and 2.

Each of the tool means 14 and 16, is seen further to be provided with ovoid-shaped depressions 34 and 36 in the region between the knurled portions 22 and 24, and the respective bases 26 and 28. When the tool is assembled as in FIG. 1 or 2, and utilized by the microsurgeon in the course of an operation, these depressions provide tactile indicia means which enable the surgeon to locate without any visual indicia the position of the center of the tool, which is a desirable aspect of the invention, since as will be shortly seen the mode of use of the tool is one wherein the first and second tool means are successively used, and in between use the instrument rotated in the hand of the surgeon. The depressions 34 and 36 facilitate this movement, and enable the surgeon to accurately position his or her hand at the center of the tool.

In accordance with a central aspect of the present invention, the first and second tool means are determinatively correlated to one another. Specifically, tool means 14, which in the present instance is associated with a female connecting base, will either be a scissors or a microprobe. Similarly, tool means 16, which in the present illustration is associated with the male connector, will be either a forceps or a needle holder. Of course, it will be appreciated that the use of male or female means may be interchanged between the two mentioned sets; but in either event, it is desired in accordance with the invention, to associate the one set with the second set of tool means for the reason that these tools are used in sequence in the microsurgeon's course of conducting the operation.

This aspect of the invention may perhaps be better understood by an example of use of the present tool. Assuming a right-handed individual, we may thus consider the case where the surgeon carries in his or her left hand, an instrument as in FIGS. 1 or 2, wherein microforceps are present at one end, and microprobe at the other. In the right hand, a second bipolar instrument of the invention is utilized, consisting of a combination of a needle holder and a microscissor. We may refer to the second instrument as "No. 2", and the first, i.e. the forceps probe combination as "No. 1".

Utilizing the No. 2 instrument, in the course of a typical operation, the needle and suture are passed through the structure being anestomosed, i.e. this is a typical surgical procedure wherein the ends, for example, of nerves or vessels are joined together. Then utilizing the No. 1 instrument, specifically the forceps, the needle and suture are picked up and pulled through so a short end remains visible from the first side of the structure. Thereafter, knot-tying is effected by utilizing the No. 1 instrument to grasp the suture, i.e. with the forceps and using the No. 2 instrument to form a loop, i.e. the needle holder, by looping the suture around the needle holder. Thereupon the needle holder is used to the short end of the suture and the latter is through the loop to form the knot, after which knots are similarly tied, for example, three such Thereupon, the No. 2 instrument is rotated with the single hand holding same, to expose the scissor's end; the suture ends are cut, leaving the knots.

At this point, the No. 1 instrument is now rotated, again with the single hand holding same, and the microprobe introduced into the lumen of the structure to insure patency, i.e. that the vessel, etc. is open and has not been inadvertently closed due to the suturing.

In FIG. 4 herein, a further aspect of the present invention is illustrated. More specifically, there is shown a further tool means 38, constituting a microprobe of relatively conventional type (details of this may be better seen in FIG. 5). In the present instance, the base of the microprobe is of the female variety, and is seen in FIG. 5 to be provided with the transverse opening 32 for the pin 30, which in the present instance, however, is present on an extension piece 40. Extension piece 40 can be hollow, knurled or the like, and is formed as shown in FIG. 4 at its one hand end, with a male connecting portion 42 which will mate with a tool means having a female end. The opposite end 44 of extension piece 40 is provided with a female end, to enable that to mate with a tool means having a male end as aforementioned.

The use of extension piece 40 enables the microsurgeon, if desired, to utilize any of the tool means aforementioned as simple unipolar instruments, by associating same with the extension piece 40. It will also be appreciated that the microprobe 38 is shown without the ovoid depressions such as 34 in FIG. 1 and 2, which are not of as great importance in a unipolar instrument; but such depressions may be present if desired.

Thus, in accordance with the further aspect of the present invention, a kit is provided for the microsurgeon, which includes a variety of first and second tool means, having the interrelationship as aforementioned, and which may include as well the extension piece 40 to enable any of the individual tool means to be used as unipolar instruments.

Typically, such a kit can include a variety of curved and straight scissors, angled and straight forceps, curved and straight needle-holders, two or more sizes of microprobes and two or more sizes of extensions.

While the present invention has been particularly described in terms of embodiments thereof, it would be understood in view of the present disclosure, that numerous variations upon the invention are now enabled to those skilled in the art, which variations yet decide within the scope of the present teaching. Accordingly, the invention is to be broadly construed and limited only by the scope and spirit of the claims now appended hereto.

I claim:

1. A multipurpose microsurgical instrument consisting of at least a pair of releasably assembled microsurgical implements, each of said microsurgical implements comprising:

a microsurgical tool;

tactile indicia associated with a grip portion of the implement by which said tool is held and manipulated, said indicia having an orientation axis discernible by the touch of a finger, said orientation axis being in a predetermined position with respect to said tool such that the orientation of said tool is known when said orientation axis is discerned by touch; and means associated with said grip portion opposite said tool for releasably engaging another one of said implements such that said microsurgical tools protrude in generally opposite directions along a common axis, said indicia being situated substantially side-by-side adjacent the center of the assembled instrument, said releasably engaging means comprising means for repeatedly locking aid implements together in the same relative position whereby said tools are in a predetermined mutually relative position such that a surgeon may assemble the instrument and correctly orient either of said said tools for use during surgery without looking at the instrument.

2. An implement in accordance with claim 1 in which said tactile indicia like on a common side of the instrument when the implements are locked together.

3. An implement of claim 2 in which said indicia are identically formed on opposite sides thereof.

4. An implement of claim 3 in which said indicia comprise depressions formed in the outer surface of the implement, said depressions being parallel to each other and extending across the implement in a direction substantially orthogonal to said axis of said tools.

5. An implement according to claim 1 in which said releasably engaging means comprises means for slidably interconnecting with a corresponding end of another of the implements.

6. An implement of claim 5 in which said locking means comprises means for snap-fitting the implements together.

* * * * *